United States Patent
Kral et al.

(10) Patent No.: US 7,459,028 B2
(45) Date of Patent: Dec. 2, 2008

(54) METHOD FOR CLEANING A LUMEN

(75) Inventors: Jude A. Kral, Twinsburg, OH (US); Michael A. Centanni, Parma, OH (US)

(73) Assignee: American Sterilizer Company, Mentor, OH (US)

( * ) Notice: Subject to any disclaimer, the term of this patent is extended or adjusted under 35 U.S.C. 154(b) by 572 days.

(21) Appl. No.: 11/180,508

(22) Filed: Jul. 13, 2005

(65) Prior Publication Data

US 2007/0071832 A1 Mar. 29, 2007

(51) Int. Cl.
*B08B 9/00* (2006.01)
*B24C 1/00* (2006.01)

(52) U.S. Cl. ............... 134/7; 134/8; 134/36; 134/37; 422/27; 451/39

(58) Field of Classification Search .......... 134/6, 134/7, 8, 22.1, 22.11, 22.12, 36, 37; 422/27, 422/28; 451/38, 39
See application file for complete search history.

(56) References Cited

U.S. PATENT DOCUMENTS

| | | | |
|---|---|---|---|
| 4,525,220 A * | 6/1985 | Sasa et al. ............... 134/21 |
| 4,707,951 A * | 11/1987 | Gibot et al. ............... 451/99 |
| 5,344,494 A | 9/1994 | Davidson et al. ......... 134/7 |
| 5,364,474 A | 11/1994 | Williford, Jr. ............ 134/32 |
| 6,468,360 B1 | 10/2002 | Andrews ................. 134/8 |
| 6,824,450 B2 | 11/2004 | Opel ..................... 451/53 |
| 6,890,246 B2 | 5/2005 | Yamaharu ............... 451/99 |
| 2002/0139395 A1* | 10/2002 | Andrews ................ 134/7 |
| 2003/0070693 A1* | 4/2003 | Stratford et al. .......... 134/7 |
| 2003/0136426 A1* | 7/2003 | Aoyagi ................. 134/22.1 |
| 2005/0106268 A1 | 5/2005 | Armstrong ............. 424/700 |

FOREIGN PATENT DOCUMENTS

| | | |
|---|---|---|
| GB | 2 398 501 | 8/2004 |
| JP | 2002-355626 | 12/2002 |
| JP | 2003-079641 | 3/2003 |
| WO | WO 03/086667 | 10/2003 |

OTHER PUBLICATIONS

Ballast Water Treatment Methods, Prince William Sound Regional Citizen's Advisory Council, Jan. 29, 2005.
"Getting the "Sand" Out of Sandblasting," Items of Interest from Dawson Macdonald, Manufacturers' Mart, 2002, no date for the document.

(Continued)

*Primary Examiner*—Michael Barr
*Assistant Examiner*—Saeed T Chaudhry
(74) *Attorney, Agent, or Firm*—Kusner & Jaffe; Michael A. Centanni

(57) ABSTRACT

A method and apparatus for removing soil from an inner surface of a lumen wall of a medical instrument are disclosed. A carrier gas entrains particles capable of sublimation at room temperature and transports the particles into and through the lumen. As the particles collide with the soil attached to the inner surface of the lumen wall, and as the particles sublime, the soil is removed from the inner surface of the lumen wall and transported out an exit of the lumen.

19 Claims, 2 Drawing Sheets

OTHER PUBLICATIONS

"Carbon Dioxide, Solid," Carbon Dioxide (CO2) Solid from Reade, Reade Advanced Materials, 1997.

"SnowBox™ Dry Ice Cleaning Station," Terra Universal.Com, Critical Environment Solutions, 2001-2004 Terra Universal, Inc.

"Cleaning Mechanisms," Carbon Dioxide Snow Cleaning, Applied Surface Technologies, 1996.

"Catalog 105—Cleaning Products," Terra Universal.Com, Critical Environment Solutions, Jul. 2001, pp. 268-283.

"Dry Ice Cleaning Equipment—Q & A Page," Phoenix Unlimited, LLC, 2005, http://www.phoenixunlimitedllc.com/quanda.asp, accessed May 16, 2005.

"Carbon Dioxide Cleaning Going Through Phases, A Panel discussion of $CO_2$ Cleaning Technology," Jul./Aug. 1999, pp. 27-34.

"SCE dry ice blasting," SCE Environmental Group, 2004.

Busnaina, Ahmed A. et al. "The Removal of Submicron Particles Using CO2 Aerosol with emphasis on post-CMP Applications" (undated), available from the Internet at least as early as Oct. 5, 2005.

* cited by examiner

METHOD FOR CLEANING A LUMEN

FIELD OF THE INVENTION

This invention relates to a method for cleaning a lumen of a medical instrument, and in particular, the lumen of an endoscope. In the method disclosed herein, a stream of particles capable of undergoing sublimation at room temperature is injected into and transported through a lumen to remove soil from the same.

BACKGROUND OF THE INVENTION

Re-usable endoscopes are commonly employed in the medical and veterinary arts. Such endoscopes, and especially the lumens thereof, are cleaned and then decontaminated after each use thus preparing the endoscope for the next use. The lumens of an endoscope can be challenging to clean.

Effective inactivation of biocontamination located on an inner wall of an endoscope lumen is accomplished only after the lumen wall is cleaned of any soil located thereon. In one approach to removing soil from the inner wall of a lumen, the inner wall of the lumen is scrubbed with a brush to remove soil adhered thereto. This approach is labor intensive and thus costly. It is therefore desirable to automate the cleaning of the lumen wall of a medical instrument such as the lumen wall of an endoscope.

Given the importance of cleaning the inner surface of a lumen wall of an endoscope prior to decontaminating the same, there is a need for an effective, inexpensive and direct method of cleaning the inner wall of an endoscope lumen.

SUMMARY OF THE INVENTION

In the present invention, particles of a material capable of sublimation at room temperature, wherein room temperature is defined herein from about 0 degrees Celsius to about 50 degrees Celsius, are injected into one end of a lumen and transported therethrough. The particles are carried in a gas carrier stream. The particles and the gas formed from the sublimation of the particles remove soil from the lumen wall. The process is continued until the lumen wall is cleared of soil, after which, any biocontamination located thereon is inactivated thus preparing the medical instrument for a subsequent use.

In the present invention, a method of cleaning a lumen wall of a medical instrument is disclosed. The method comprises the steps of creating a directional flow of a carrier gas that entrains particles of a material capable of sublimation at room temperature; directing the carrier gas and particles into a first end of a lumen of the medical instrument; and, removing at least a portion of soil from the lumen wall.

In addition, the present invention discloses an apparatus capable of removing soil from an inner surface of a lumen wall of a medical instrument. The apparatus comprises a source of particles capable of sublimation at room temperature. The apparatus further comprises a carrier gas wherein the carrier gas entrains and transports the particles into and through the lumen. The velocity of the carrier gas may also be sufficient enough to transport a portion of the particles to an end of the lumen of the medical instrument prior to sublimation.

One advantage of the present invention is the provision of an automated system to remove soil from an inner surface of a lumen wall of a medical instrument such as an endoscope.

Another advantage of the present invention is the provision of a method to clean a lumen wall of a medical instrument in which the cleaning particles used undergo sublimation at room temperature.

Another advantage of the present invention is the provision of a method to clean a lumen wall of a medical instrument such that the cleaning medium turns into a gas thus obviating the need to collect and treat the cleaning medium.

A yet further advantage of the present invention is the provision of a method for cleaning a lumen wall that leaves the lumen wall dry after cleaning.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE INVENTION

Broadly stated, a method and apparatus for cleaning the inner surface of a lumen of a medical instrument such as a lumen of an endoscope are disclosed. The cleaning of the inner surface of such a lumen is effected by transporting, in a gaseous carrier stream, solid particles through the lumen wherein the particles are capable of undergoing sublimation at room temperature while within the lumen or while in contact with the lumen's inner surface. In a preferred embodiment of the present invention, solid carbon dioxide particles are transported through the lumen by a carrier gas. The dislodged soil is transported by the carrier gas out an exit end of the lumen. Hence, in this approach, the cleaning particles simply disappear during the cleaning process leaving only the soil to be collected and disposed of.

Figure 1:
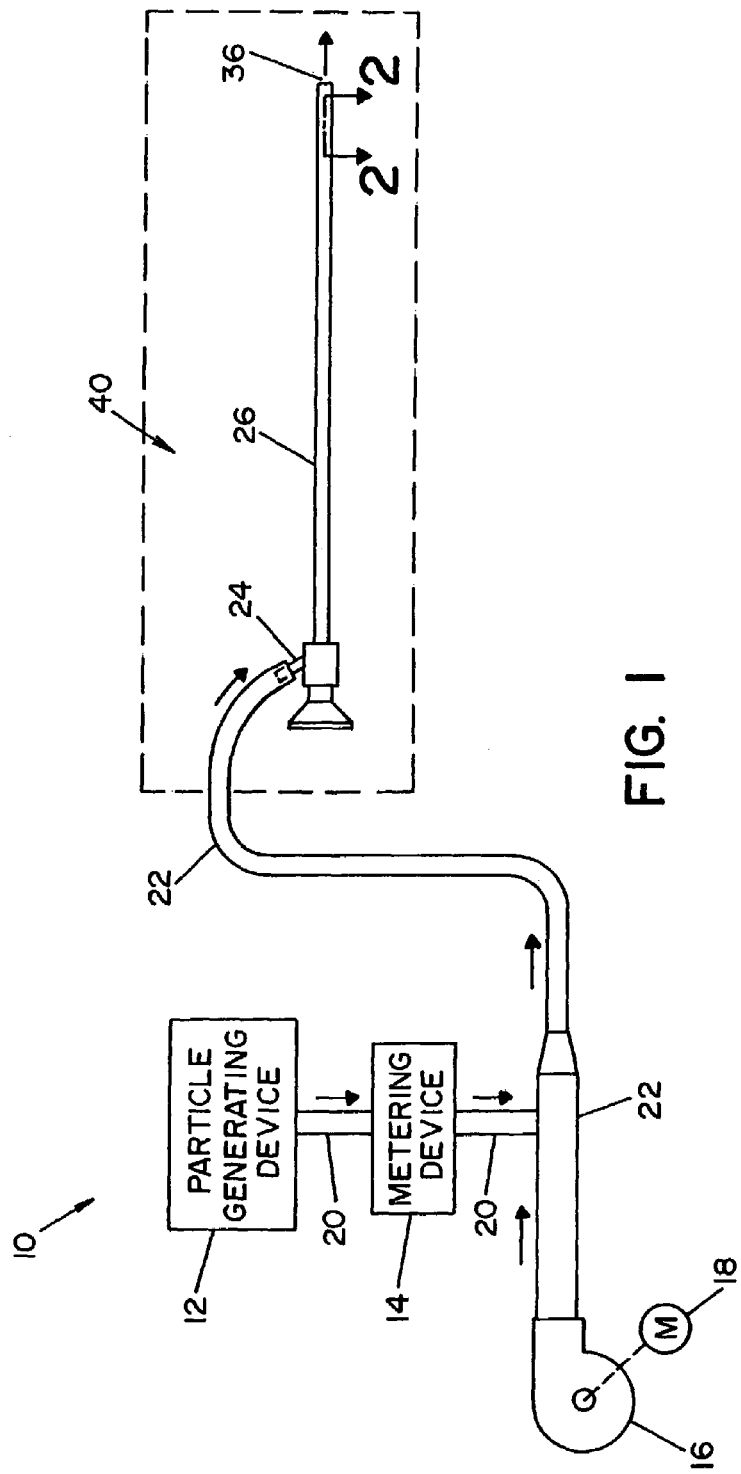
FIG. 1 is a diagram of a lumen of a medical instrument and an apparatus to remove soil from the inner surface of the lumen according to the present invention.

Referring now to the drawings wherein the showings are for the purposes of illustrating a preferred embodiment of the invention only and not for purposes of limiting the same, FIG. 1 shows a cleaning system 10 according to a preferred embodiment of the present invention. Cleaning system 10 includes a particle generating device 12, a particle metering device 14 (e.g., a metering valve) and a blower 16, driven by motor 18. Particle generating device 12 is connected to particle metering device 14 through tube 20. Particle metering device 14 is connected to conduit or hose 22 through conduit or tube 20. Hose 22 extends from an outlet port of blower 16 to an inlet port 24 of a lumen 26 located on a medical instrument 40.

Figure 2:
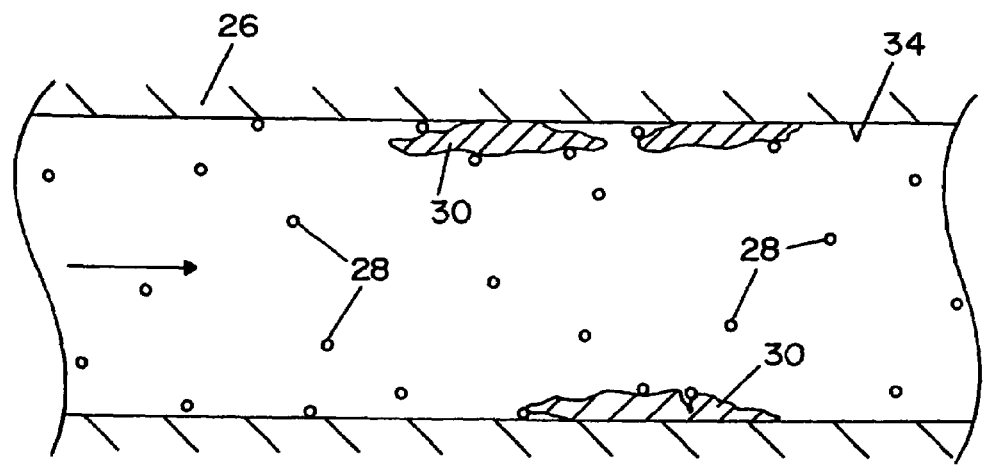
FIG. 2 is sectional view taken along line 2-2 of the lumen showing soil adhered to the inner surface of the lumen.

FIG. 2 is a sectional view taken along line 2-2 of lumen 26 showing soil 30 attached to an inner surface 34 of lumen 26. Also shown in FIG. 2 are cleaning particles 28 flowing through lumen 26. The direction of flow of the carrier gas and cleaning particles is in the direction of the arrow shown in FIG. 2.

Figure 3:
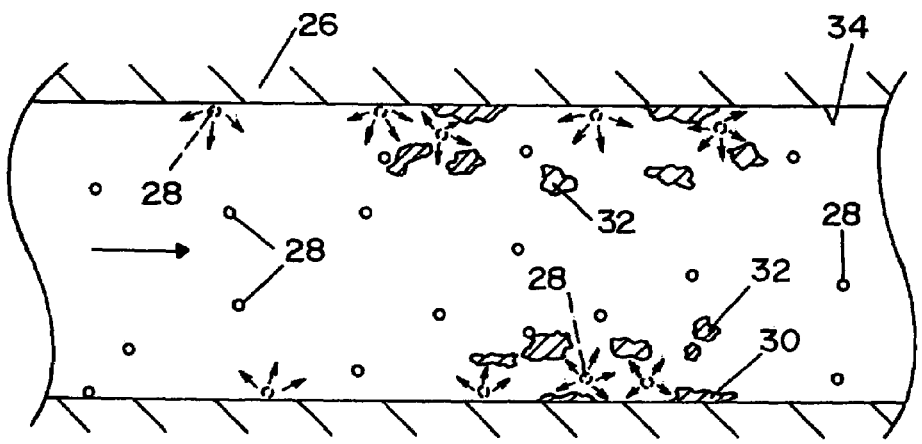
FIG. 3 is a sectional view taken along line 2-2 of the lumen showing the removal of soil adhered to the inner surface of the lumen according to a method of the present invention.

FIG. 3 is a sectional view taken along line 2-2 of lumen 26 showing soil 30 being removed from inner surface 34 of lumen 26 according to the present invention.

Turning now to the operation of cleaning system 10, reference is made to FIG. 1 wherein particle generating device 12 generates particles capable of sublimation at room temperature. Sublimation is a process whereby a solid material turns directly into a vapor without first turning into a liquid. One example of such a particle is solid carbon dioxide particles or "dry ice" particles. Although the invention is not be limited to the use of solid carbon dioxide particles as cleaning particles 28, the invention will be described as using the same because of the low cost of solid carbon dioxide particles and the ease of commercially making solid carbon dioxide particles.

After particle generating device 12 generates cleaning particles 28, e.g., solid carbon dioxide particles, cleaning particles 28 are transported through tube 22 to metering device 14. Metering device 14 meters a predetermined amount of cleaning particles 28 into hose 22 through tube 20. Metering device 14 allows one to change the number concentration of cleaning particles 28 that are transported into and through lumen 26. Parameters that might lead one to change the number concentration of cleaning particles 28 introduced into hose 22 might include the amount of soil 30 attached to inner surface 34 of lumen 26, the type of soil attached to inner surface 34 of lumen 26 and thus, the adhesive forces binding soil 30 to inner surface 34, the length of lumen 26 or the speed of the transporting carrier gas.

In the example shown in FIG. 1, the carrier gas is air and the air stream is generated by blower 16 driven by motor 18. As cleaning particles 28 are introduced into hose 22, cleaning particles 28 are transported through hose 22 to inlet port 24 of lumen 26 of medical instrument 40. Cleaning particles 28 are then transported into, and in one embodiment, through lumen 26 by the carrier gas.

Referring now to FIG. 2, cleaning particles 28 are introduced into lumen 26 having soil 30 disposed on inner surface 34 of lumen 26. As cleaning particles 28 are transported through lumen 26, cleaning particles 28, and/or the gas produced therefrom, remove soil 30 from inner surface 34 of lumen 26, as shown in FIG. 3.

The carrier gas that transports cleaning particles 28 can be any gas and may optionally include, for example, a deactivating gas or vapor. Examples of such deactivating gases or vapors include gases such as ozone, a chlorine or bromine containing gas or vaporized hydrogen peroxide. In this respect, one may clean inner surface 34 of lumen 26 and simultaneously deactivate inner surface 34 of any biocontamination residing thereon. Thus, the cleaning and deactivation steps are reduced to one operation.

With no intent to be bound, it is believed that soil 30 may be removed from inner surface 34 by one or a combination of the following mechanisms. In one instance, it is believed that kinetic energy of cleaning particles 28 is transferred directly to soil 30 thus dislodging soil 30 from inner surface 34 of lumen 26. Once dislodged, the carrier gas sweeps dislodged soil 32 through lumen 26 of medical instrument 40 and out exit 36 of lumen 26 (see FIGS. 1 and 3). In another instance, it is believed that as cleaning particles 28 contact inner surface 34 of lumen 26, the rate of production of carbon dioxide gas is accelerated as a result of the warming of cleaning particles 28. It is believed that this rapid production of carbon dioxide gas then blows soil 30 off inner surface 34 of lumen 26. As in the first instance, dislodged soil 32 is then carried through lumen 26 of medical instrument 40 and out exit 36 of lumen 26.

The kinetic energy of cleaning particles 28 can be varied and speeds of up to and in excess of 300 meters per second can be used to clean inner surface 34 of soil 30. In one embodiment, the speed of the carrier gas is about 305 m/s. In another embodiment, the speed of the carrier gas ranges from about 0.01 m/s up to about 305 m/s. In another embodiment, the speed of the carrier gas ranges from about 0.1 m/s up to about 275 m/s. It will be appreciated that in the event high speeds, such as 300 m/s, are used, blower 16 may be insufficient to provide such high speeds. In this case, other means to create such high speeds of the carrier gas may be required.

Cleaning particles 28, such as solid carbon dioxide particles, ranging in size from about 5 microns up to about 0.5 cm in diameter may be used to clean soil 30 from the inner surface 34 of lumen 26 of medical instrument 40. In another embodiment, cleaning particles 28 ranging in size from about 10 microns up to about 0.1 cm in diameter may be used. In another embodiment, cleaning particles 28 having a diameter of about 10 microns are used. In another embodiment, cleaning particles 28 having a diameter of about 20 microns are used.

An advantage of using cleaning particles 28 that sublime at room temperature to clean the inner surface 34 of lumen 26, is that cleaning particles 28 disappear during or after use. Thus, the only residual material that must be collected and disposed of is dislodged soil 32. In addition, another advantage realized by using a material that sublimes at room temperature is that inner surface 34 of lumen 26 remains dry during and after cleaning. Any water vapor initially located within lumen 26 is swept out of lumen 26 by the dry carrier gas. This minimizes the chance of further biocontamination of inner surface 34 after the cleaning operation.

Commercial, solid carbon dioxide cleaning stations are commercially available. For example, TERRA UNIVERSAL (Anaheim, Calif.) manufactures a solid carbon dioxide cleaning station (the SnowBox™ Dry Ice Cleaning Station). This station is capable of maintaining a dry nitrogen atmosphere within a chamber, thus minimizing problems that relate to condensation. This station is also capable of producing solid carbon dioxide particles small enough (5 microns in diameter) to be used to clean inner surface 34 of lumen 26. This station can also develop carrier gas speeds of up to about 305 m/s.

In one embodiment, air or dry air is used as the carrier gas. In another embodiment, nitrogen gas or dry nitrogen gas is used as the carrier gas. The use of helium gas or dry helium gas as the carrier gas is also contemplated.

In some cases, the entire length of a lumen cannot be cleaned in one step. In these instances, the dry ice particles should be introduced into each accessible port that leads into a lumen of the endoscope. Thus, in this approach, each section of a lumen is cleaned separately.

One can also clean the exterior surface of the medical instrument (e.g., an endoscope) of soil with a jet of particles of a material capable of sublimation at room temperature (e.g., dry ice particles). In this regard, the carrier gas and particles are directed at an exterior surface of the medical instrument until at least a portion of the soil adhered to the exterior surface of the medical instrument is removed therefrom.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method for simultaneously cleaning and deactivating an inner surface of a lumen of a medical instrument, comprising the steps of:

creating a directional flow of a carrier gas that includes a gas or vapor for effecting deactivation of biocontamination;

generating particles of a material capable of sublimation at room temperature;

regulating a metering device to entrain the particles in the carrier gas, wherein said metering device is regulated to change concentration of the particles entrained in the carrier gas according to at least one of the following parameters:
(a) amount of soil adhered to the inner surface of the lumen,
(b) type of soil adhered to the inner surface of the lumen,
(c) length of the lumen, and
(d) velocity of the carrier gas;

directing said carrier gas and particles into a first end of the lumen of the medical instrument; and maintaining flow of said carrier gas and particles until at least a portion of soil adhered to the inner surface of the lumen is removed therefrom.

2. The method of claim 1, wherein the material capable of subliming comprises carbon dioxide particles.

3. The method of claim 1, wherein the carbon dioxide particles have particle sizes ranging from about 5 microns up to about 0.5 cm.

4. The method of claim 1, wherein the carrier gas has velocities of up to about 305 meters/second.

5. The method of claim 1, wherein the carrier gas includes air.

6. The method of claim 1, wherein the carrier gas includes nitrogen gas.

7. The method of claim 1, wherein said gas or vapor for effecting deactivation of biocontamination includes ozone, a bromine or chlorine containing gas, or vaporized hydrogen peroxide.

8. The method of claim 1, wherein the medical instrument is an endoscope.

9. The method of claim 1, wherein the method further comprises:
regulating said metering device to direct only said carrier gas into said first end of the lumen of the medical instrument, after at least a portion of the soil adhered to the inner surface of the lumen is removed therefrom.

10. The method of claim 1, wherein said metering device is regulated to change concentration of the particles entrained in the cater gas according to (1) the length of the lumen and (2) the velocity of the carrier gas.

11. A method for simultaneously cleaning and deactivating an exterior surface of a medical instrument, comprising the steps of:

creating a directional flow of a carrier gas that includes a gas or vapor for effecting deactivation of biocontamination;

generating particles of a material capable of sublimation at room temperature;

regulating a metering device to entrain the particles in the carrier gas, wherein said metering device is regulated to change concentration of the particles entrained in the carrier gas according to at least one of the following parameters:
(a) amount of soil adhered to the external surface of the medical device,
(b) type of soil adhered to the external surface of the medical device, and
(c) velocity of the carrier gas;

directing said carrier gas and particles at an exterior surface of the medical instrument; and maintaining flow of said carrier gas and particles until at least a portion of soil adhered to the exterior surface of the medical instrument is removed therefrom.

12. The method of claim 11, wherein the material capable of subliming comprises carbon dioxide particles.

13. The method of claim 12, wherein the carbon dioxide particles have particle sizes ranging from about 5 microns up to about 0.5 cm.

14. The method of claim 12, wherein the carrier gas has velocities of up to about 305 meters/second.

15. The method of claim 12, wherein the carrier gas includes air.

16. The method of claim 12, wherein the carrier gas includes nitrogen gas.

17. The method of claim 12, wherein said gas or vapor for effecting deactivation of biocontamination includes ozone, a bromine or chlorine containing gas, or vaporized hydrogen peroxide.

18. The method of claim 12, wherein the medical instrument is an endoscope.

19. The method of claim 11, wherein the method further comprises:
regulating said metering device to direct only said carrier gas at said exterior surface of the medical instrument, after at least a portion of the soil adhered to the inner surface of the lumen is removed therefrom.

* * * * *